(12) United States Patent
Sliwa et al.

(10) Patent No.: US 10,349,965 B2
(45) Date of Patent: Jul. 16, 2019

(54) PRESSURE SENSING OF IRRIGANT BACKPRESSURE FOR ALIGNING DIRECTIONAL MEDICAL DEVICES WITH TARGET TISSUE

(71) Applicant: St. Jude Medical, Atrial Fibrillation Division, Inc., St. Paul, MN (US)

(72) Inventors: John W. Sliwa, San Jose, CA (US); Zhenyi Ma, Santa Clara, CA (US); Stephen A. Morse, Menlo Park, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 15/816,863

(22) Filed: Nov. 17, 2017

(65) Prior Publication Data

US 2018/0132886 A1    May 17, 2018

Related U.S. Application Data

(63) Continuation of application No. 13/837,964, filed on Mar. 15, 2013, now Pat. No. 9,848,899.

(51) Int. Cl.
| | | |
|---|---|---|
| *A61B 17/32* | (2006.01) | |
| *A61B 18/18* | (2006.01) | |
| *A61B 18/14* | (2006.01) | |
| *A61N 7/00* | (2006.01) | |
| *A61B 90/00* | (2016.01) | |
| *A61B 18/00* | (2006.01) | |

(52) U.S. Cl.
CPC .. *A61B 17/320068* (2013.01); *A61B 18/1492* (2013.01); *A61B 18/18* (2013.01); *A61B 90/37* (2016.02); *A61N 7/00* (2013.01); *A61B 2018/00577* (2013.01); *A61B 2090/064* (2016.02); *A61B 2090/0807* (2016.02); *A61B 2090/3782* (2016.02); *A61B 2090/3784* (2016.02); *A61B 2217/007* (2013.01); *A61N 2007/0047* (2013.01)

(58) Field of Classification Search
CPC ........ A61M 1/0058; A61M 2205/3334; A61M 2205/3344; A61M 2205/3331; A61M 2205/0002; A61M 2205/0003; A61B 18/1492; A61B 18/18; A61B 2090/378; A61B 2090/3782; A61B 2018/00577; A61B 2217/007; A61B 2018/00636; A61B 2018/00738; A61N 7/00
See application file for complete search history.

(56) References Cited

U.S. PATENT DOCUMENTS

| | | |
|---|---|---|
| 4,641,649 A | 2/1987 | Walinsky et al. |
| 4,892,102 A | 1/1990 | Astrinsky |
| 4,945,912 A | 8/1990 | Langberg |
| 5,228,442 A | 7/1993 | Imran |
| 5,231,995 A | 8/1993 | Desai |

(Continued)

*Primary Examiner* — Bradley J Osinski
*Assistant Examiner* — Nilay J Shah
(74) *Attorney, Agent, or Firm* — Wiley Rein LLP

(57) ABSTRACT

Systems and methods for aligning directionally operable medical devices with and upon target tissue. Systems and methods for aligning medical devices such as directional ablation catheters to and upon target tissue by monitoring irrigant backpressure. The current disclosure provides solutions to the problem of rotationally or angularly aligning a directional medical device toward tissue.

10 Claims, 5 Drawing Sheets

(56) References Cited

U.S. PATENT DOCUMENTS

| | | | |
|---|---|---|---|
| 5,242,441 A | | 9/1993 | Avitall |
| 5,246,438 A | | 9/1993 | Langberg |
| 5,263,493 A | | 11/1993 | Avitall |
| 5,281,213 A | | 1/1994 | Milder et al. |
| 5,281,217 A | | 1/1994 | Edwards et al. |
| 5,281,218 A | | 1/1994 | Imran |
| 5,293,868 A | | 3/1994 | Nardella |
| 5,327,905 A | | 7/1994 | Avitall |
| 5,354,297 A | | 10/1994 | Avitall |
| 5,487,385 A | | 1/1996 | Avitall |
| 5,582,609 A | | 12/1996 | Swanson et al. |
| 5,785,704 A | | 7/1998 | Bille et al. |
| 6,171,303 B1 | * | 1/2001 | Ben-Haim ............ A61B 5/0215 606/15 |
| 6,394,956 B1 | | 5/2002 | Chandrasekaran et al. |
| 2005/0187546 A1 | * | 8/2005 | Bek .................... A61B 18/1492 606/41 |
| 2010/0041986 A1 | | 2/2010 | Nguyen et al. |

* cited by examiner

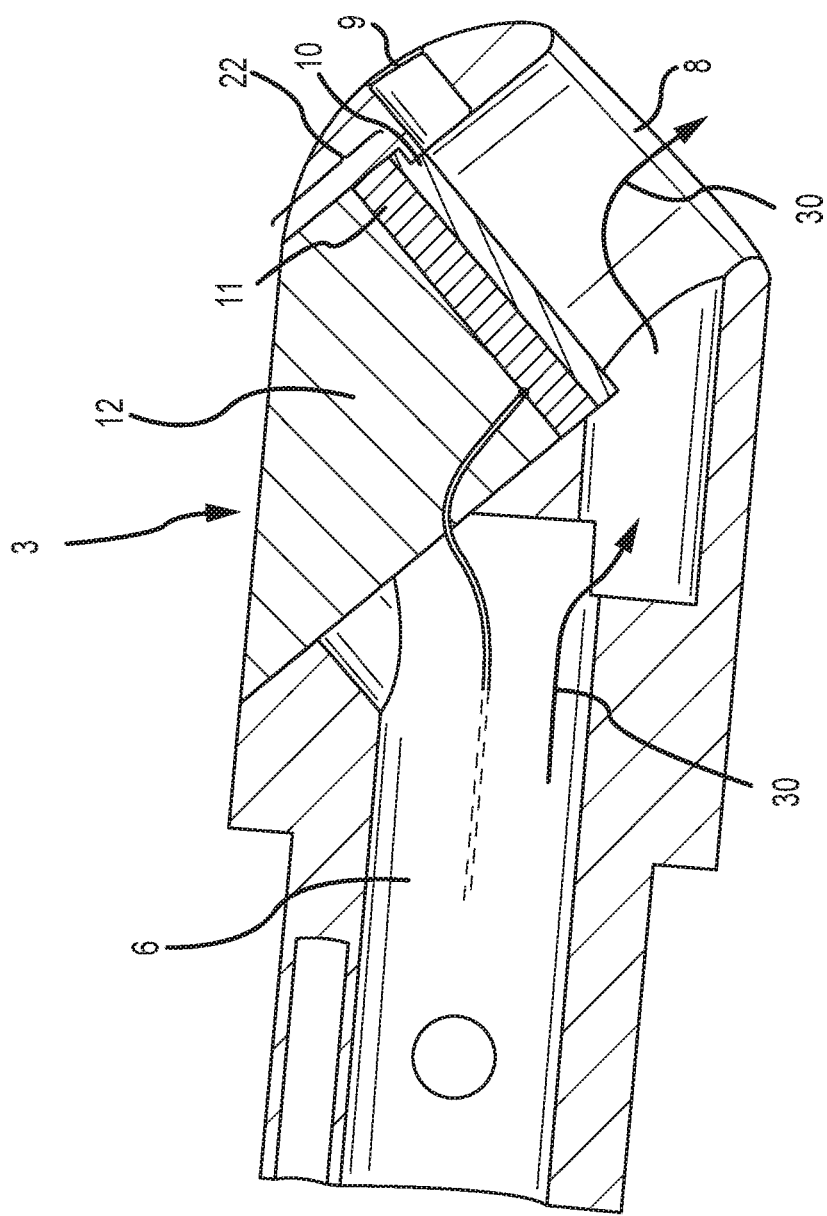

PRESSURE SENSING OF IRRIGANT BACKPRESSURE FOR ALIGNING DIRECTIONAL MEDICAL DEVICES WITH TARGET TISSUE

CROSS-REFERENCE TO RELATED APPLICATIONS

This application is a continuation of U.S. application Ser. No. 13/837,964, filed 15 Mar. 2013 (the '964 application), now U.S. Pat. No. 9,848,899. The foregoing application is hereby expressly incorporated by reference as though fully set forth herein.

BACKGROUND

The present disclosure relates generally to systems and methods for aligning medical devices with target tissue. In particular, the instant disclosure relates to systems and methods for aligning medical devices, such as directional ablation catheters, to target tissue by monitoring irrigant backpressure. Directional medical devices require positioning the active end, e.g. ablation or sensing end, toward the tissue. In the context of ablation catheters, for example, such monitoring of irrigant backpressure can be utilized to more effectively direct therapy towards a target tissue and/or to ensure that the device is properly aligned to adequately evaluate the efficacy of the therapy via an imaging or sensing element, such as an electrode or transducer.

Catheters are common medical tools that have been used for many years. Such devices are employed in medical procedures, for example, to examine, diagnose, and treat while positioned at a specific location within the body that would otherwise be inaccessible without more invasive procedures. In such procedures, a catheter is typically first inserted into a vessel near the surface of the body and then guided to a specific location within the body. Once positioned at the desired location, the catheter may be used, for example, to convey an electrical stimulus to a selected location within the human body and/or to monitor various forms of electrical activity within the body.

Using catheters in medical procedures, such as cardiac ablation, for the treatment of certain types of cardiac arrhythmia has become increasingly more common. Catheter ablation is based on the idea that by ablating (i.e., destroying) abnormal tissue areas in the heart, the heart's electrical system can be altered to return the heart to normal rhythm. During catheter ablation therapy, the catheter is typically inserted into an artery or vein in the leg, neck, or arm of the patient and then threaded, sometimes with the aid of a guide wire or introducer, through the vessels until a distal tip of the catheter reaches the desired location for the medical procedure in the heart.

During conventional catheter ablation procedures, an energy source is in contact with cardiac tissue to heat the tissue and create a permanent scar or lesion that is electrically inactive or non-contractile. These lesions are designed to interrupt existing conduction pathways commonly associated with arrhythmias within the heart. The particular area for ablation depends on the type of underlying arrhythmia. The use of RF ablation electrode catheters for ablating specific locations within the heart has been disclosed in, e.g., U.S. Pat. Nos. 4,641,649, 5,228,442, 5,231,995, 5,263,493, and 5,281,217.

Many conventional ablation procedures use a single electrode secured to the tip of an ablation catheter. It has become increasingly more common to use multiple electrodes affixed to the catheter body, however, with such ablation catheters often containing a distal tip electrode and a plurality of ring electrodes as disclosed in, e.g., U.S. Pat. Nos. 4,892,102, 5,228,442, 5,327,905, 5,354,297, 5,487,385, and 5,582,609.

Many conventional ablation catheter tips may be placed upon the tissue and activated to deliver ablative action regardless of the catheter orientation with respect to rotation about the catheter tip axis. That is, because many of these devices are omnidirectional in their function, the orientation of the catheter tip relative to the target tissue is not a significant factor in their efficacy. For example, some conventional RF tips include an RF electrode that is symmetric about its longitudinal axis in order to ablate uniformly without regard to tip rotation. In such cases, the rotational alignment of the catheter tip does not have a significant impact, and thus there is often no rotational alignment requirement for the catheter.

A variety of energy sources can be used to supply the energy necessary to ablate cardiac tissue and create a permanent lesion. Such energy sources include direct current, laser, microwave, and high intensity ultrasound. Because of problems associated with the use of DC current, radiofrequency (RF) alternating current has become a common source of energy for many ablation procedures. The use of RF energy for ablation has been disclosed, e.g., in U.S. Pat. Nos. 4,945,912, 5,242,441, 5,246,438, 5,281,213, 5,281,218, and 5,293,868.

In contrast to catheters that are rotationally symmetric about their longitudinal axis, some emerging catheter designs deliver unidirectional therapy or sensing and thus must be rotationally aligned with the target tissue to be ablated and are configured to deliver therapy or sensing in one or more specific aligned directions. In some emerging procedures, for example, such catheters are used for delivering at least one of a diagnostic or therapeutic function in a directional manner because the inherent operation of the catheter tip is directional rather than omnidirectional. An example of a directional therapeutic function is a directed laser beam that ablates in one direction. For example, the directed laser beam may be used for directing ablation therapy from a side or away from an end of the tip towards a target tissue site. An example of a directional diagnostic or sensing function is a diagnostic ultrasound pinger directed towards a target tissue location for pinger ultrasonic-echo provided feedback on the formation of an ablation lesion or other tissue characteristics.

In some cases, the catheter tip may have both ablative as well as diagnostic functionality, one or both of which may be directional in nature, requiring rotating or angulating the tip to aim towards a particular position on the tissue. This aiming of the catheter can be referred to as directional rotational or angular alignment. It should be understood that once a catheter is placed against a target tissue surface it develops a contact force regardless of its rotational or angular orientation or need thereof. Alignment is about aiming or directing whereas contact-force is about contact force or pressure regardless of the tip's alignment.

In the context of ultrasonic pingers, for example, it is often necessary to have good alignment such that the pinging transducer beam is directed towards and squarely into the tissue and the pinger contacts that tissue consistently with at least a few grams of force. If the tip containing the pinger is also an RF ablating tip then a good ablator tissue contact force of 20-30 grams minimum is needed such that the ablation current passes into the tissue with a reasonably low electrical contact impedance. Although the terms "contact force" and "contact pressure" are used interchangeably herein, it should be understood that the force divided by the actual tissue contact area yields the contact pressure. In some RF ablation procedures, for example, a tip contact force of about 20 grams minimum may be required for reproducible RF contact to tissue.

Determination of contact force between the catheter ablator tip and the target tissue has long been indirectly done by (a) monitoring the electrical contact impedance at the RF ablation frequency, and in some cases also (b) monitoring the apparent deformed shape of the catheter, such as in an X-ray fluoroscopy image. More recently, a number of direct optical methods utilizing optical fibers have been suggested such as that of Endosense Inc. in which a number of interferometer optical fibers are used to monitor tip-spring displacements (tip bending and axial deflections), which can be used to derive tip forces. Approaches which utilize three or more such optical interferometer fibers plus dedicated LEDs and photodiodes can become expensive to manufacture, are fragile, and do not leave much room for other important catheter components, such as catheter steering wires and fluid lumens.

Other means for determining tissue contact and catheter alignment are pinging acoustic transducers mounted in or adjacent the catheter tip to acoustically detect lesion volume and tissue-contact, as well as indirectly tissue contact force. The acoustic pulse-echo approach may also permit a clinician to discern the lesion state at specific tissue depths when time-delay pulse-echo range data is available. This also allows for direct measurement of tissue thickness or organ proximity

BRIEF SUMMARY

The current disclosure provides solutions to the problem of rotationally or angularly aligning a directional medical device toward tissue. In general, disclosed herein are methods and systems for aligning a directional medical device towards tissue by measuring the irrigant backpressure of a constant flow of irrigant as a function of tissue blockage. Good alignment causes good blockage, which causes higher backpressure.

One embodiment is a system for aligning a medical device with target tissue, the system including an elongate medical device, a fluid pump, at least one pressure sensor, and a processor. The system may also be packaged as part of a kit.

The elongate medical device includes a proximal region and a distal region. The distal region may have at least one directional therapeutic or diagnostic component. The medical device also includes an irrigant delivery lumen having a proximal end and a distal end, wherein the distal end of the irrigant delivery lumen has an exit port at the distal end of the distal region of the medical device. Operably connected to the irrigant delivery lumen is a fluid pump that supplies fluid to the irrigant delivery lumen, preferably at a constant known rate. The pressure sensor measures variations in fluid (e.g., irrigant) backpressure. The pressure sensor may be coupled to the fluid pump. In other embodiments, the pressure sensor may be located at the distal end of the irrigant delivery lumen or in the tip of the medical device.

In some embodiments the processor computes and reports variations in fluid backpressure during device manipulation. When the medical device is properly aligned with the target tissue, the exit port coaxially emitting both the irrigant and the sensor beam and/or directional therapy is better blocked by the target tissue and the irrigant backpressure significantly increases. The processor may also provide feedback such as lesion depth or steampop warnings.

In other embodiments, the medical device includes at least one therapeutic component and at least one diagnostic component. The therapeutic component may be a tissue ablating component. In some embodiments, the ablating component may be an ultrasound (e.g. HIFU of high intensity ultrasound) or RF ablation element. The ablating component may also utilize microwave energy, laser energy, or cryogenic energy. The ablating component may be unidirectional or omnidirectional. The processor may sense when an ablation steam pop is about to happen and shut off or reduce the power of the ablating component.

The irrigant delivery lumen in the medical device may also serve as a vacuum pathway. Alternatively, in some embodiments, the medical device includes a second lumen that defines a vacuum pathway operably coupled to a flow control apparatus. The vacuum lumen pathway has a proximal end and a distal end. The distal end of the vacuum lumen pathway has an exit port at the distal end of the catheter such that it can suction the tip upon the tissue thereby contributing to securing it in place.

Another embodiment is an ablation catheter apparatus. The ablation catheter apparatus has an elongated catheter body extending longitudinally between a proximal portion and a distal portion along a longitudinal axis. The ablation catheter apparatus further includes an irrigant delivery lumen disposed longitudinally within the elongated catheter body. The irrigant delivery lumen has a proximal end and a distal end. In some embodiments, the ablation catheter also has a vacuum lumen disposed longitudinally within the elongated catheter body. The ablation catheter further has a distal member disposed adjacent to the distal portion of the elongated catheter body. The distal member may be an ablation element. The ablation catheter apparatus also has at least one pressure monitoring element that senses fluid backpressure. In some embodiments, the pressure monitoring element is disposed on a fluid pump operably coupled to the irrigant delivery lumen. In other embodiments, there may be a plurality of pressure monitoring elements on the ablation catheter apparatus, such as one or two on the tip of the catheter, one or two on the distal portion of the ablation catheter, and/or one or two within the irrigant delivery lumen. A processor is operably connected to the at least one pressure monitoring element, wherein the processor determines whether the ablation element is aligned to a target tissue. The processor may determine whether the ablation element is rotationally or angularly aligned with the target tissue, i.e., directionally aligned with the target tissue.

The present disclosure also discusses methods of detecting the orientation of medical devices such as mapping or ablating catheters. In one exemplary embodiment, a method of detecting orientation includes the steps of:

a) moving the medical device toward a target tissue b) delivering fluid via an irrigant delivery lumen; and c) measuring a change in backpressure as the tip of the medical device moves toward and upon the target tissue. An increase in backpressure during tissue contact indicates directional alignment of the tip with the target area.

In other embodiments, an exemplary method of detecting orientation includes the steps of:

a) flowing irrigant fluid out of a medical device tip at a first lower rate (e.g., about 2-3 ml/min) wherein the expected backpressure for the current lower flow rate (e.g. 2 ml/min) is known for the non-tissue contact condition (e.g., about 2 psi) and the full-tissue contact aligned condition (e.g., about 9 psi), and wherein the medical device tip comprises an ablating element;

b) bringing the outflowing medical device tip into contact with tissue;

c) manipulating the tissue-tip contact angles and contact forces to maximize the irrigant backpressure and achieve optimal alignment at the first lower flow rate; and d) delivering ablation at a higher, cooling flow rate (e.g., about 17 ml/min) while continuing to maintain good alignment by continuing to maximize the now higher backpressure (about 22 psi at 17 ml/min expected).

In other embodiments, an exemplary method of detecting orientation includes the steps of:

a) flowing irrigant fluid out of a medical device tip;
b) moving the medical device tip toward the target tissue;
c) measuring and analyzing backpressure; and
d) rotating and angulating the tip against tissue to achieve peaked backpressure greater than the minimum value desired.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 3A is a cross-sectional view showing an embodiment of a backpressure-monitoring distal tip region.

DETAILED DESCRIPTION

As used herein "proximal" refers to the direction away from the body of a patient and towards a clinician. Furthermore, as used herein "distal" refers to the direction toward the body of a patient away from the clinician.

As used herein "aligning" refers to the act of facing a directional medical device toward tissue such that a directional component of the device, whether therapeutic or diagnostic, can operate favorably while having a face-on view of at least some adjacent or nearby target tissue. Alignment of the tip may involve both rotational angulation about the tip axis as well as angulation on a rotational axis normal to that. (i.e. rotational left/right angulation and forward/back angulation) As disclosed herein, aligning is aided by the maximization of irrigant backpressure emanating from a directional fluid port, codirectional with the directional sensor or directional therapy, which has been found to result in the desirable face-on state. The device is designed such that if the port is manipulated to become face-on to tissue, the directional component is also face-on or otherwise satisfactorily aimed toward tissue. Typically an aligned device will be in partial or complete contact with tissue, but actual physical contact between the device and the tissue is not a requirement, and the teachings herein can be employed to good advantage even with the device and tissue in a non-contact or light-contact state.

Reference will now be made in detail to certain embodiments of the present invention, examples of which are illustrated in the accompanying drawings.

Figure 1:
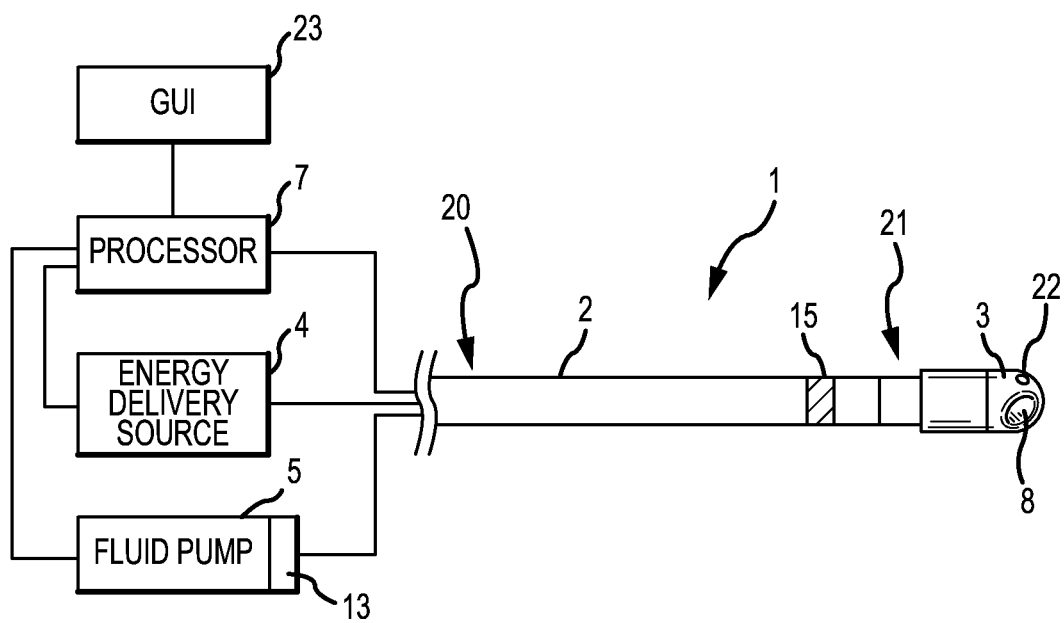
FIG. 1 is a schematic diagram of a system for aligning a medical device with target tissue in accordance with an illustrative embodiment.

FIG. 1 is a schematic diagram of a system for aligning a medical device 1 with target tissue. As shown in FIG. 1, the system generally includes a medical device 1, an energy delivery source 4, a fluid pump 5, a processor 7, and a pressure sensor 13.

As shown in FIG. 1, medical device 1, energy delivery source 4, and fluid pump 5 are operably coupled to processor 7. As described in further detail below, processor 7 is configured to determine whether medical device 1 is aligned to a target tissue (e.g., to determine whether medical device 1 is rotationally, angularly, and/or directionally aligned with the target tissue), for example by monitoring irrigant fluid backpressure.

FIG. 1 depicts pressure sensor 13 coupled to the output line of fluid pump 5. It should be understood, however, that pressure sensor 13 can be located elsewhere, such as integral with pump 5, within irrigant delivery lumen 6, or at or near exit port 8, without departing from the spirit and scope of the instant teachings. It is desirable, however, to locate pressure sensor 13 at or near fluid pump 5, particularly when medical device 1 is disposable, as doing so minimizes the disposable device 1 cost.

Medical device 1 has an elongated flexible catheter body 2 including a proximal section 20 and a distal section 21 including a distal tip region 3. Medical device 1 can further include a ring electrode 15, which can be employed as a localization and/or pacing element as generally known in the art.

Medical device 1 can also be connected to energy delivery source 4. The energy delivery source 4 can be an ablation energy source, such as an RF generator. Thus, in some embodiments, medical device 1 includes an energy delivery element. Of course, distal tip region 3 can be configured as a metallic ablation element (that is, as a tip electrode). Alternatively, distal tip region 3 can incorporate both a directional pulse-echo ultrasonic transducer 22 (e.g., for ablation feedback) and an RF ablation element.

Figure 2:
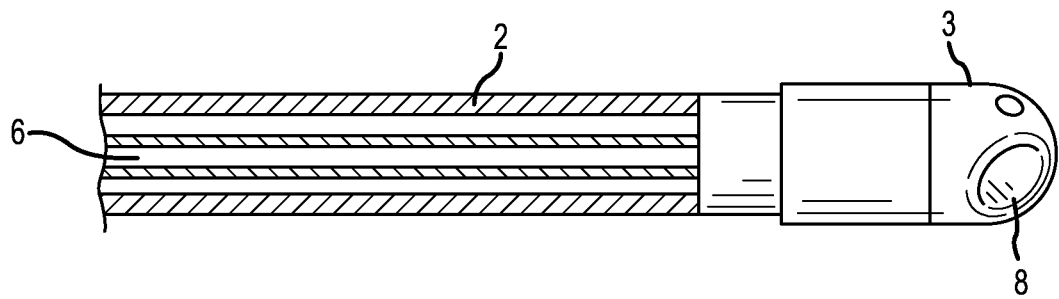
FIG. 2 is a partial cross-sectional view showing an exemplary catheter including a distal tip region configured to measure changes in irrigant backpressure for aligning the catheter with a target tissue.

FIG. 2 is a partial cross-sectional view of a medical device 1 and a distal tip region 3 thereof. As further illustrated in FIG. 2, medical device 1 includes an irrigant delivery lumen 6 therethrough. As the ordinarily skilled artisan should appreciate, fluid pump 5 can be coupled to irrigant delivery lumen 6 in order to supply irrigant and/or cooling fluid, such as saline, thereto. In one aspect, fluid pump 5 can be a positive displacement pump, such as a CoolPoint™ peristaltic pump. Such a positive displacement pump delivers a constant average flowrate such that the average backpressure changes in direct relation to the tips outflow tissue blockage at various states of alignment.

As further shown in FIG. 2, irrigant delivery lumen 6 has a proximal end and a distal end, with the distal end extending to the outer surface of distal tip region 3 through at least one common coaxial irrigant and ultrasound beam exit port 8 out of which both irrigant and a directed ultrasonic pinging transducer beam are directed. Of course, it should be understood that irrigant delivery lumen 6 is representative, and that the medical device 1 can include any number of such lumens.

It should be understood that a directed ultrasonic pinging transducer beam must be properly aligned toward and upon tissue for maximum echo-reception efficacy. As shown in FIG. 2 and in some embodiments, the ultrasonic beam exit port 8 is fixedly oriented at approximately a 45 degree angle to the longitudinal axis of medical device 1. In other embodiments, the ultrasonic beam exit port 8 can be fixedly oriented at other desired angles. When medical device 1 is a catheter, an angle of about 45 degrees allows catheter distal tip region 3 to be used to perform end-on or side-on lesions or lesions at in-between angles and still obtain ultrasonic feedback.

Regardless of its location, pressure sensor 13 measures the backpressure of fluid inside irrigant delivery lumen 6 and relays this measurement to processor 7. Any suitable communication methodology can be employed, including, for example, a communications cable that interconnects processor 7 and pressure sensor 13 or a wireless communications protocol. Likewise, pressure sensor 13 may provide analog or digital output. In some embodiments it is also desirable for pressure sensor 13 to report the irrigant backpressure at a sampling rate of at least 4 readings/second or faster with an accuracy of at least +/−1 psi. Of course, higher sampling rates are contemplated, as are the application of filters or other signal processing to the output of pressure sensor 13. If the pump is a pulsatile peristaltic pump, then the flow rate is pulsatile and the backpressure is pulsatile around an average constant backpressure so the cyclic variations in backpressure due to the pump are superimposed upon the detected average backpressure. This is not a major issue, because the cyclic pressure increases its average and instantaneous values with increasing tissue blockage in an identical manner as if it were a truly constant flow rate (i.e., not pulsatile).

Pressure sensors 13 known in the art include those based on deforming mechanical or MEMs-type metallic, silicon or piezo diaphragms. In some embodiments, irrigant delivery lumen 6 can utilize low-creep elastomers or braiding, such that the elasticity of lumen 6 does not significantly modulate the varying backpressure changes due to varying alignment or pump pulsatility.

Processor 7 can be configured to perform several functions. First, processor 7 can interpret the irrigant backpressure, as measured by pressure sensor 13, as an indicator of the tissue contacting alignment between tip region 3 and tissue. Processor 7 can also interpret feedback from a directional pinging ultrasonic transducer 22 included in distal tip region 3 for the purpose of providing lesion feedback, such as lesion-depth or steam pop warnings, tissue proximity measurements (before contact), and/or (indirectly and qualitatively) tip contact force monitoring as implied by backpressure increase. In some embodiments, circuitry, for example analog circuitry, internal to the medical device 1 performs same functions as processor 7.

As can be further seen by reference to FIG. 1, a graphical user interface ("GUI") 23 is electrically coupled to the processor 7. The GUI 23 may be configured to provide information from which a graphical representation of an internal structure within the body may be created. The GUI 23 may include data input devices such as touch screens, buttons, switches, keypads, magnetic readers and other input devices. The GUI 23 may also include data output devices such as data and image screens, lights, audio warnings and other output devices The output of processor 7 can be presented to the operator (e.g., using GUI 23) as a real time assessment of the tip alignment and lesioning progress when the tip region 3 comprises an ablating element and pinger. The information may additionally or alternatively be utilized by the processor 7 itself as part of a feedback control system that can operate with or without operator intervention. For example, processor 7 may be configured to measure the backpressure and modulate or enable/disable energy delivery source 4 in response thereto.

The teachings herein can be employed to good advantage in connection with an ablation catheter having an omnidirectional RF ablator tip in combination with a directional pinger to ultrasonically assess lesion formation. To render the directional pinger effective, the tip must be directed or aimed toward tissue such that the ultrasonic pinger beam passes into the ablating target tissue beneath the contacting tip where the lesion is to be made. Thus, it is desirable to be able to align an ablation element having a directional feedback sensor toward and upon target tissue by applying codirected irrigation and measuring backpressure. By rotating and/or tilting the ablation element, one can remotely (e.g., without direct observation or imaging aids) squarely aim the ablating element and its directional ultrasonic sensor at the target tissue to be ablated. For omnidirectional RF ablation, the omnidirectional ablation tip should contact tissue and the directional ultrasonic pinger, which will assess the lesion, should be directed or aligned toward the tissue target. Pinger return signals are strongest and clearest with tissue contact as compared to a state in which the pinger is not in contact and is instead spaced apart from the tissue.

FIG. 3A depicts distal tip region 3 of an exemplary RF ablation catheter. In one embodiment of the invention, an irrigation fluid such as saline is delivered from a fluid pump 5 into and through irrigant delivery lumen 6; in FIG. 3A, the irrigant 30 is shown entering tip region 3 itself. The irrigant 30 then exits distal tip region 3 at the codirected irrigant/ultrasound exit port 8. Exit port 8 also serves as an ultrasonic beam window for ultrasonic energy emitted by transducer 22.

In other embodiments the distal tip region 3 includes a plurality of exit ports, with at least one of the exit ports serving as both an alignment irrigant port and an ultrasonic beam port. In such embodiments, the exit port that also serves as an ultrasonic beam window is typically the largest of the exit ports, which allows for a large backpressure signal to be developed during alignment to tissue of that specific port when only that port is blocked by tissue. An additional smaller port 9 aimed away from the tissue target might, for example, be used to bleed any steam bubbles from the tip.

In some embodiments the ultrasound pulse-echo pinging ultrasonic transducer 22 is configured to provide lesioning feedback to the practitioner. Ultrasonic transducer 22 can include an acoustic matching layer 10 and a piezoceramic layer 11 having top and bottom electrodes (not shown for purposes of clarity of illustration). Piezoceramic layer 11 may be a PZT layer. Ultrasonic transducer 22 can also be potted and acoustically and mechanically backed by an acoustic backer material 12. Acoustic backer material 12 may be a known lossy tungsten/epoxy ultrasonically attenuative backer material or any other suitable backer material.

In one embodiment, exit port 8 is spatially directionally aligned coaxially with a directional diagnostic monitoring ultrasound beam. The codirected exit port 8 and ultrasonic beam may be centered (not shown) within the distal tip region 3 such as for forming end-on lesions. The codirected exit port 8 may be angled away from the center of the distal tip region 3 such as at 45 degrees (as shown in FIG. 3A) such that directional lesion feedback is provided for a range of tissue-contact angles from end-on to side-on.

Figure 3B:
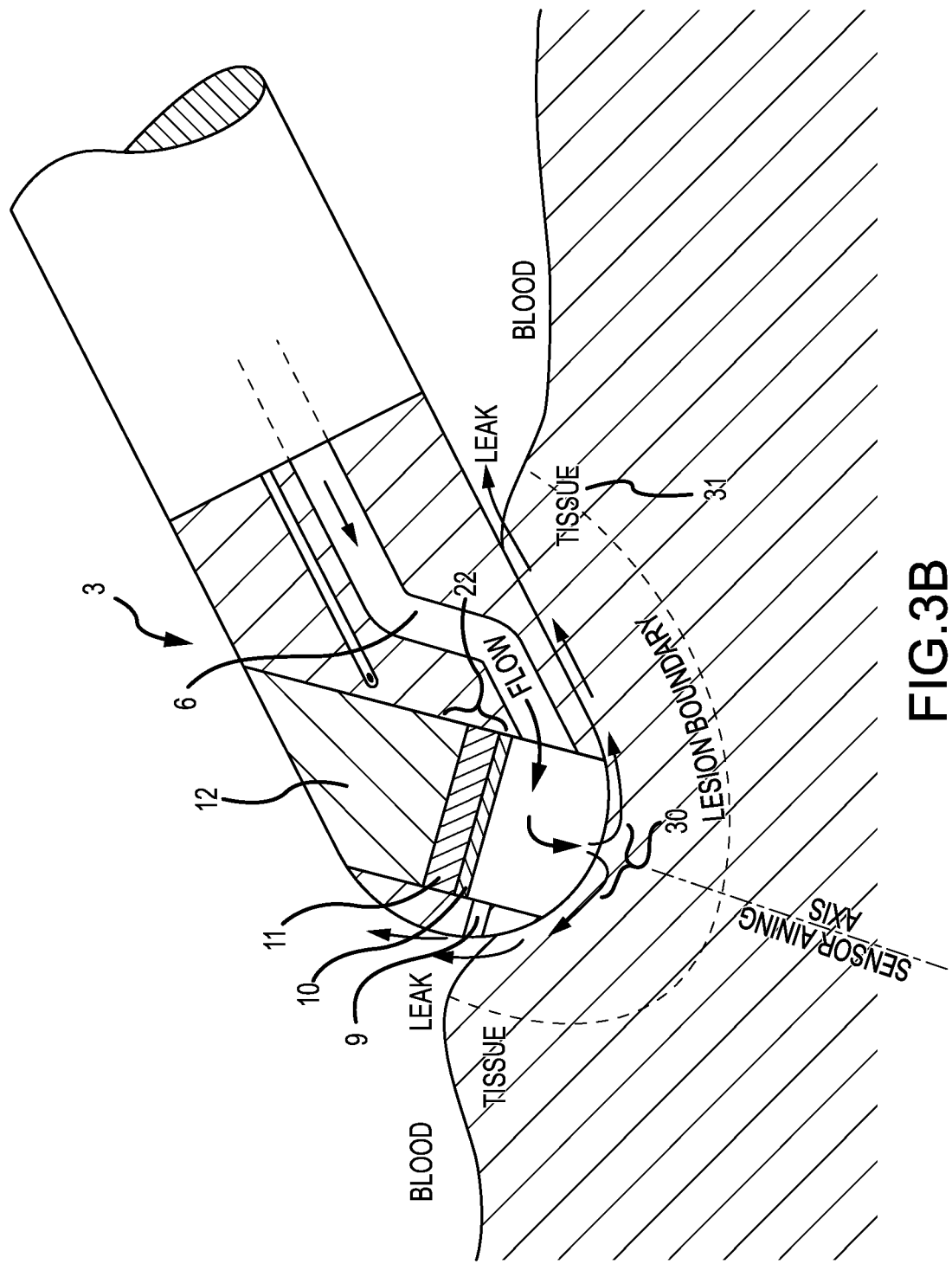
FIG. 3B is a schematic diagram showing an embodiment of a backpressure monitoring tip contacting target tissue.

In FIG. 3B, for example, distal tip region 3 is illustrated as immersed in blood and resting upon cardiac tissue 31. As shown in FIG. 3B, the outflowing irrigant 30 that leaks past port 8 sitting upon and aligned face-on to target tissue serves to also cool tip region 3. The irrigant may be degassed, sterile water or saline, typically at or below room temperature before entry into the warmer body. The emitted irrigant fluid suppresses near-surface tissue (and tip) heating, thus reducing char and driving lesions deeper.

In the embodiment depicted in FIG. 3B, ultrasound transducer 22 directs its pinging beam along a given beam line during lesioning, such that the resulting echogram is an echo-depth versus lesion elapsed time echogram. To accomplish this, tip region 3 should be rotationally or angularly aligned by the user so that the ultrasound beam is pointed into the tissue being lesioned. In some embodiments the ultrasonic transducer 22 is configured for 2D or 3D ultrasonic imaging, which would require that the transducer is either wobbled (e.g., angularly scanned) or is electronically scanned, such as in the case of a multi-element (not shown) phased array transducer.

Alignment between tip region 3 and tissue can be sensed using the backpressure of the irrigant flowing through lumen 6. That is, as distal tip region 3 approaches and seats itself upon the target tissue with exit port 8 facing the tissue, the irrigant flow emanating from exit port 8 is obstructed and experiences an incrementally increased backpressure. Peaked or maximal increases in backpressure indicate the best alignment of the tip region 3 with the target tissue at that flow rate, because the adjacent tissue best fits edges of port 8 and seals them as best it can. Because a positive-displacement pump, such as the CoolPoint™ peristaltic pump, forces a fixed flow rate of irrigant through irrigant delivery lumen 6 and out exit port 8, any obstruction of exit port 8 must cause irrigant backpressure to rise in accordance with the degree of obstruction.

An irrigant flow rate of a few ml/min (usually about 2 to about 5 ml/min) is historically always maintained during RF ablation, even when RF ablation is turned off, in order to prevent blood backflow into irrigant delivery lumen 6 and tip region 3 which could result in clotting. Once RF ablation starts, a higher user-settable cooling flow is typically automatically provided which may be, for example, in the range of about 10 to about 17 ml/min. The higher flow helps prevent tip charring and tissue steam pops. The body's maximal irrigant (saline) intake rate is about 17 ml/min from a physiological point of view. In other embodiments, a pump with a stepping motor or diaphragm pump can be used to create the irrigant flow.

As exit port 8 becomes obstructed by the target tissue, the backpressure measured in the irrigant delivery lumen 6 will rise to a maximum value, which represents both the best alignment of port 8 axis and ultrasound beam into the tissue and the best possible tissue sealing of the outflow given whatever tip-force is present. Higher tip contact force will result in a higher peak alignment pressure due to the more forceful tissue sealing. The tip alignment to maximize the backpressure involves the physician-familiar tilting and rotation of tip region 3 upon tissue as by for example, manipulating a catheter handle (push, pull, rotate) or by manipulating the tip-bending steering wires located within the catheter.

Upon achieving peak backpressure at the existing flow rate, port 8 and its emanating ultrasound beam are more or less normally or squarely directed into the tissue situated directly in front of the tip-tissue contact region.

The backpressure magnitude developed by the inventive contacting codirectional tip is an indirect indicator of the above discussed tissue contact force or pressure. The reason is that the irrigant is delivered at a constant flow rate so that outflow obstructions of the tip's outflow port causes higher and higher backpressures as the obstruction is more and more forceful, i.e., as the contact force gets higher during alignment. Thus we include in the scope the use of our alignment backpressure as a contact-force sensor as well.

It is understood in the field of ultrasound transducers that the face of the transducer should be seated squarely against the tissues to get a view directly inwards and that that square or generally orthogonal orientation also results in the strongest ping echoes. It will thus be appreciated that pulse-echo operation of the transducer at this angular geometry with good alignment will produce strong echo reflections. After alignment one may therefore obtain a pre-lesion echogram (e.g., multiple images at that position over a period of seconds), start the RF ablation, and continue to sample echograms during ablation to monitor lesion progress. Time-interleaved RF ablation and ultrasound sampling is desirable in order to minimize electrical interference therebetween. After RF ablation is complete, one may gather additional echo lines versus time and wait for a steady settled state of echo contrast, if necessary.

During the ablation one may also monitor the fluid backpressure to assure that proper alignment and valuable echograms are maintained. Even when the backpressure in the irrigant delivery lumen is maximized, all of the irrigant fluid leaks at the somewhat sealed interface between the distal tip region 3 and target tissue, albeit at the raised backpressure indicating good alignment and contact. The leaks must occur because a positive-displacement fluid delivery pump is used and the flow rate is always maintained despite moderate backpressures occurring from the obstruction by the target tissue. Desirably, however, even moderate changes in backpressure can be used to align the distal tip region 3 with the target tissue. The backpressures employed for the alignment are well below those which would stall or stop the pump or be dangerous to the patient or practitioner.

The amount and direction of the measured changes in backpressure can be conveyed to the operator of the catheter via an audible tone. In another embodiment of the invention, the measured change in backpressure can be conveyed to the operator via a color-changing or dynamic icon on a 3D medical navigation tool, such as the Ensite™ Velocity™ System available from St. Jude Medical, Inc. Other forms of feedback, such as haptic feedback, are also contemplated. In another embodiment as discussed further herein, the achievement of the desired minimum backpressure for a particular flow rate (i.e., having good alignment of the pinger into the intended lesion) is used to enable (or disable if bad) the ability to ablate.

In some embodiments, backpressure variations are used to achieve tissue alignment at one or more user-settable flow rate. The flow may be low, high, steady, or pulsatile, and DC unidirectional outwards or AC outwards/inwards. Typically the tip alignment will be via manual catheter manipulation; however, robotic manipulation is within the spirit and scope of the present teachings.

Once the ablating element is aligned with the target tissue, exit port 8 may also serve as a suction tip-clamping port. In one embodiment, exit port 8 is coupled to a source of varying suction pressure, such as a suction pump. Activation of the source of varying suction pressure results in a pressure differential between distal tip region 3 and the suction lumen, drawing distal tip region 3 towards the tissue and stabilizing the device relative to the tissue. In some embodiments, irrigant delivery lumen 6 can be interchangeably coupled to both a source of fluid and a source of varying suction pressure via a valve. Alternatively, irrigant delivery lumen can be manually coupled to either a source of fluid or a source of varying suction pressure to switch between a suction stabilizing mode and an irrigating mode. In still other embodiments, a dedicated suction lumen and/or dedicated suction port can be provided.

As used herein, "suction" means negative pressure relative to the blood pool surrounding tip region 3. Ideally, the suction port suctions fluid (irrigant) or small limited amounts of blood. It is preferred not to allow gas into the irrigant line, but instead maintain it as fluid-filled. By preventing gas from entering the irrigant line, gas bubbles that may dampen desired backpressure signals can be eliminated or minimized. During a suction clamping phase, greater suction flow-resistance corresponds to the best tissue seal of port 8 and also the best alignment. Maintenance of the suction vacuum may also be employed to assure proper aiming of a directional outflow port/suction port or even of a suction port alone, and therefore proper aiming of the directional ultrasonic pinger sensor. Outflowing irrigant backpressure peaking is employed to align the tip 3 to tissue; thereafter, lumen 6 fills with liquid irrigant, which may then optionally have a clamping suction pulled on it. In many cases, tip/tissue surface cooling during ablation will be required, thus irrigant outflow must continue during such ablation out of at least one of the exit ports or via recirculating coolant lines within the medical device 1. If a vacuum suction port is employed, it may be an independent port from exit port 8. Pressure maximization of exit port 8 helps to ensure that the vacuum port and exit port 8 are facing the tissue.

In one embodiment, exit port 8 has a circular transverse cross-section. However, as a person of skill in the art will appreciate, the shape of exit port 8 can be designed and fabricated having diverse and/or differing shapes and cross-sectional areas, for example, having an oval, square, rectangular, slit, or any other regular or irregular shape, area, and cross-section. In another embodiment, port 8 may be substantially circular with a plurality of narrow off-shoots or appendages extending radially outwardly to form a star-like configuration. The physical edges of the port 8 can be radiused as depicted in FIG. 3A to minimize the risk of tissue trauma.

In another embodiment, the ablating element or tip region 3 is an electrically conducting or metallic radiofrequency (RF) ablating element. The RF ablating element is usually a conductive metal having, in one embodiment, a convex generally bullet shaped surface as shown in FIGS. 3A and 3B. The metal may be any bulk or coated electrically conductive metal or a metal alloy which is biocompatible and also has a reasonable electronic work-function such as one or more of platinum, platinum iridium, palladium, rhodium, gold, silver, carbon/graphite, titanium or nickel-titanium alloy such as Nitinol. In some embodiments, it may be desirable to include a layer of biocompatible metal material covering a nonbiocompatible metal conductive underlying metal such as platinum plated titanium or Nitinol. The acoustic matching layer 10 of FIGS. 3A and 3B may itself be electrically conductive or may be coated with an electrically conductive thin metal film. In this manner, the face of the matching layer 10 may also act as an ablating RF electrode across the small saline gap in between the electrode and the tissue.

In another embodiment, medical device 1 may incorporate other types of directional or omnidirectional ablating elements suitable for forming ablation lesions such as a microwave transmitter, a cryogenic element, an optical element, or an acoustic transducer such as, for example a high intensity focused ultrasound (HIFU) transducer. At least one of the therapeutic or diagnostic/monitoring devices in the distal tip region 3 is directional in nature, such that the teachings herein regarding tip alignment can be employed to good advantage.

Figure 4:
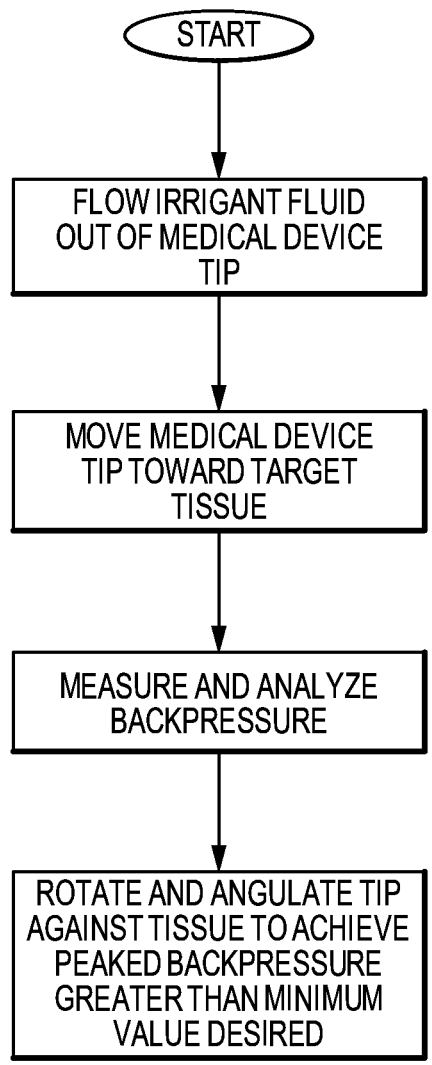
FIG. 4 is a flow diagram showing an illustrative method of aligning a catheter with a target tissue in accordance with an illustrative embodiment.

FIG. 4 is a flow diagram that schematically illustrates an exemplary method of aligning a medical device with a target tissue, e.g., cardiac tissue, during a clinical or diagnostic procedure, e.g., an ablation procedure, in accordance with an exemplary embodiment of the present disclosure. The distal tip region 3 approaches the target tissue via practitioner and/or robotic manipulation. Some irrigation fluid emanates from exit port 8 even before ablation starts and before any tissue contact is made. As the distal tip region 3 gets closer to and finally contacts the target tissue, the fluid backpressure will incrementally significantly increase with increasing tissue contact force and improving alignment. Before physical contact the pressure increases are minimal. The backpressure increases several fold (e.g., between about 2 times to 5 times, for example) upon good alignment and contact, even in the case of low flow rates of a few ml/min if a positive displacement pump is employed with an outflow port of about 1.5 mm in diameter. Processor 7 measures the changes in backpressure and provides information as to whether distal tip region 3 should be further manipulated to achieve better alignment. The large majority of pressure increase happens after some tissue contact is achieved.

In one embodiment, the method of detecting orientation includes the steps of:

(a) flowing irrigant fluid out of the catheter tip region 3 at a first lower rate (e.g., 2-3 ml/min) whose backpressure is known for the no-tissue contact state (e.g., 2 psi) and full-tissue contact state (e.g., 9 psi);

(b) bringing the outflowing tip region into contact with tissue;

(c) manipulating the tissue-tip contact angles and contact forces via a control handle to maximize the irrigant backpressure increase to achieve the best alignment at the first lower flow rate at the anticipated backpressure of roughly 9 psi; and (d) delivering ablation at a higher, cooling flow rate (e.g., 17 ml/min) while continuing to maintain good alignment by continuing to maximize the now-higher backpressure (e.g., approx. 22 psi at 17 ml/min for best alignment) at the now higher flow rate.

When the irrigant backpressure is maximized by proper alignment, at least a minimum contact force of the tip to tissue is achieved, otherwise the pressurized irrigant would hydraulically lift the tip completely off of the tissue. Thus, in the state of best alignment, there is a peaked backpressure with irrigant leaking out of an imperfect port/tissue seal at the set flow rate of a peristaltic positive displacement pump. The use of a positive displacement pump is preferred as it increases its backpressure markedly given increasing flow resistance downstream.

The method of detecting orientation of the ablation catheter may also include synchronizing the delivery of therapy (or diagnostic feedback) with the instantaneous motion of the heartbeat or the breathing pattern. The irrigant backpressure, even during maximized static alignment, still has a cyclic nature due to the continued motion of the heart walls and the lungs. By using these cyclic backpressure waveforms the practitioner may deliver therapeutic and/or diagnostic functionality in synchronization with these patterns if doing so is advantageous from a clinical point of view.

Figure 5:
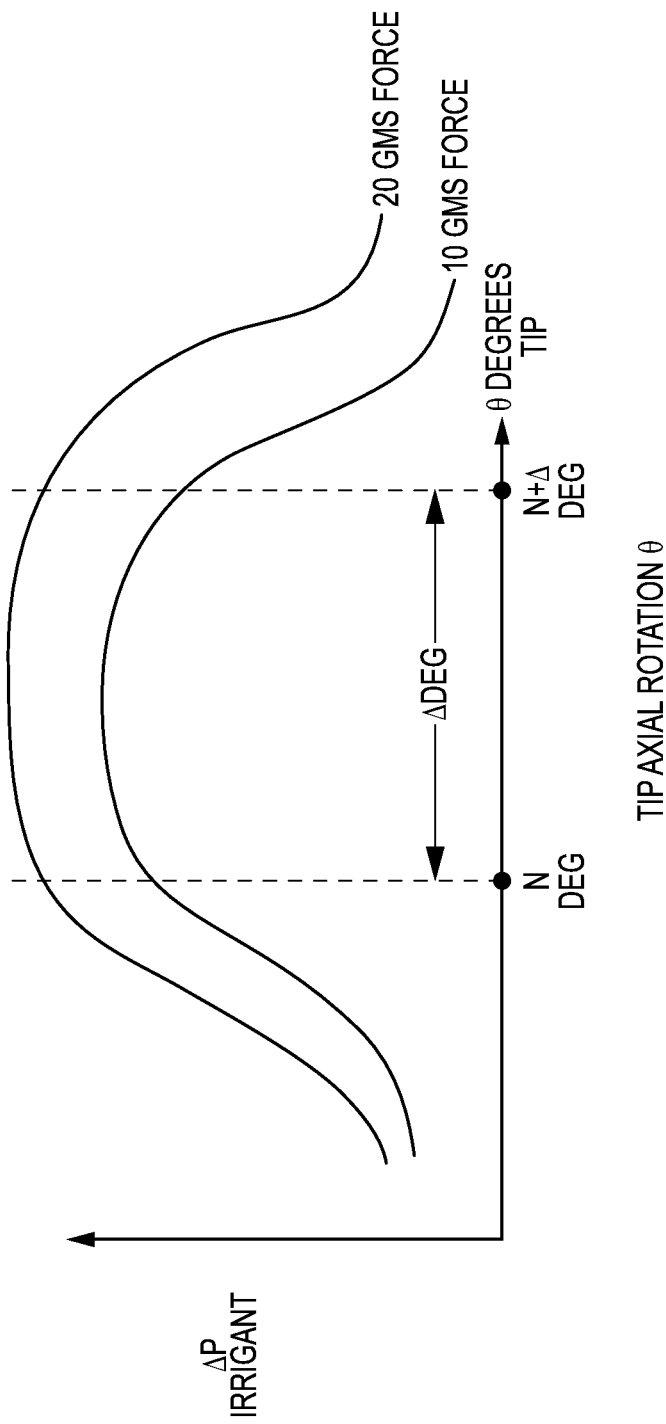
FIG. 5 is a graph illustrating the behavior of the change in backpressure as the ablation catheter tip rotates around the primary axis. Two plots are shown for two different tip forces.

FIG. 5 is a graph illustrating the behavior of the change in measured backpressure versus the change in the distal tip region 3 rotational angle θ about the primary axis of the catheter 1. The two plots represent two different forces applied by the distal tip region 3. The peak of the curves, i.e., the area between N° and N°+ΔN°, represents the peak backpressure range wherein monitoring echograms will have the best signals returning. It is at the angles that achieve the peak of the curves wherein the ultrasound beam is aligned relatively squarely (e.g., face-on) with the target tissue to be ablated.

At the higher 20 gms tip force as shown in FIG. 5, a higher increase in backpressure is achieved. With the higher increase in backpressure, there is a larger rotational range for aligning the ultrasound beam with the target tissue. This is because the tissue is more deformed by the higher load which creates a better seal at the tip. Greater application of distal tip 3 force on the tissue leads to more deformed tissue and a wider angular range for aligning the ultrasound beam with the target. Making contact with the tissue directly in front of the tip exit port 8 can be done well despite the tissue being substantially indented and the exit port 8 not being perfectly square with the local overall tissue wall. In some embodiments, a tip contact force of about 20 grams or greater can be employed as this has been demonstrated to result in good RF contact whether the tip is ablating end-on, side-on or at an in-between angle to target tissue. Higher forces (at the same power/flow), e.g., 40 grams, will increase the lesion depth. Too high of a force, e.g. over 100 gms, may traumatically puncture the myocardium particularly for end-on tip contact to tissue.

The floppy soft thin tissues of the atrial chambers result in quite wide angular ranges (+/−15-20 deg rotation or tilt angle) over which the port sealing to tissue can be achieved with a large backpressure whereas the harder tissues of the ventricles result in narrower angular ranges (+/−5-10 deg rotation or tilt angle) of maximal backpressure achievement. This follows directly from the ease with which tissue is partially extruded into the exit port 8 by the contact force (and is pushed outwards by the flow). A good alignment with peaked backpressure roughly correlates with a contact force necessary to accomplish that sealing. Backpressure peaking provides at-least qualitative assurance of the presence of a minimum contact force to provide ablation efficacy. An embodiment includes the use of achieved backpressure, a known outflow rate and a known tip/port shape/size to look up or compute an approximate tissue contact force. Such force correlations may be developed on the bench or in an animal lab. In that manner the tip region 3 can be used to create lesions, monitor their depth, prevent steam pops and assure the minimal force of 20 gms or so enables the ablation to be undertaken.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A system for rotationally aligning a medical device with a target tissue, comprising:
    a medical device having a proximal region and a distal region, the distal region comprising a distal tip and at least one directional therapeutic or diagnostic component, the medical device further comprising:
    an irrigant delivery lumen having a proximal end and a distal end, wherein the distal end of the irrigant delivery lumen comprises an exit port at the distal tip of the distal region of the medical device, and wherein the irrigant delivery lumen exit port is coaxially aligned with the directional component, further wherein the directional component comprises an ultrasonic transducer, and wherein irrigant exits the irrigant delivery lumen at the exit port, wherein the exit port is also an ultrasonic beam port for the ultrasonic transducer;
    a fluid pump operably configured to supply a fluid to the irrigant delivery lumen;
    at least one pressure sensor configured to measure fluid backpressure in the irrigant delivery lumen; and
    a processor or circuitry capable of reporting increases in fluid backpressure during manipulation of the medical device, wherein the processor is configured to determine that the ultrasonic transducer is rotationally aligned with and upon the target tissue based upon the at least one pressure sensor sensing a peak fluid backpressure from the exit port.

2. The system of claim 1, wherein the distal region of the medical device comprises the at least one directional diagnostic component and the at least one directional therapeutic component.

3. The system of claim 1, wherein the at least one pressure sensor is coupled to the medical device.

4. The system of claim 1, wherein the at least one pressure sensor is coupled to the fluid pump.

5. The system of claim 1, wherein the irrigant delivery lumen is also operably connected to a vacuum or suction source to secure the tip to the tissue.

6. The system of claim 1 wherein the fluid pump is a positive displacement pump configured to maintain a substantially constant flow rate, and wherein the backpressure increases as the flow output of the fluid pump is obstructed.

7. The system of claim 1, wherein the processor is capable of sensing when an ablation steam pop is about to happen and shutting off or reducing a power of an ablating component.

8. An ablation catheter apparatus comprising:
    an elongated catheter body extending longitudinally between a proximal portion and a distal portion along a longitudinal axis;
    the distal portion comprising at least one directional ablator or diagnostic component, wherein the at least one directional component is an ultrasonic transducer, and an irrigant outflow port directionally coaxially aligned with the at least one directional component;

an irrigant delivery lumen disposed within the catheter body and terminating at the irrigant outflow port, wherein the irrigant outflow port is also an ultrasonic beam port for the ultrasonic transducer;

at least one pressure monitoring element, wherein the at least one pressure monitoring element senses irrigant fluid backpressure caused by varying tissue blockage of the irrigant outflow port;

and a processor or circuitry operably connected to the at least one pressure monitoring element, wherein the processor is configured to determine that the ultrasonic transducer is rotationally aligned with and upon a target tissue based at least in part upon the at least one pressure sensor sensing a peak fluid backpressure from the irrigant outflow port.

9. The ablation catheter apparatus of claim 8, wherein the at least one pressure monitoring element is coupled to the ablation catheter.

10. The ablation catheter apparatus of claim 8, wherein the at least one pressure monitoring element is coupled to a fluid pump.

* * * * *